United States Patent [19]

Parker

[11] Patent Number: 5,637,077

[45] Date of Patent: Jun. 10, 1997

[54] CUSTOM-MOLDED ANKLE BRACE

[75] Inventor: A. Bruce Parker, Charlotte, N.C.

[73] Assignee: Smith & Nephew Casting, Inc., Memphis, Tenn.

[21] Appl. No.: 549,947

[22] Filed: Oct. 30, 1995

[51] Int. Cl.⁶ ....................................................... A61F 5/00
[52] U.S. Cl. ..................... 602/8; 602/27; 602/6
[58] Field of Search .................. 602/5–8, 23, 27–29, 602/60–62, 65

[56] References Cited

U.S. PATENT DOCUMENTS

| | | |
|---|---|---|
| D. 307,054 | 4/1990 | Johnson, Jr. . |
| 2,103,942 | 12/1937 | Gillin . |
| 2,169,203 | 8/1939 | Hinchliff . |
| 2,267,070 | 12/1941 | Baldwin . |
| 2,480,849 | 9/1949 | Gersh et al. . |
| 2,512,081 | 6/1950 | Young . |
| 2,761,443 | 9/1956 | Parker . |
| 2,940,884 | 6/1960 | White . |
| 2,960,984 | 11/1960 | Parker . |
| 3,085,569 | 4/1963 | Cook et al. . |
| 3,557,156 | 1/1971 | Enneper . |
| 3,631,855 | 1/1972 | Fehlau . |
| 3,683,903 | 8/1972 | Fox et al. . |
| 3,826,252 | 7/1974 | Laico . |
| 3,882,857 | 5/1975 | Woodall, Jr. . |
| 3,900,024 | 8/1975 | Lauber et al. . |
| 3,923,049 | 12/1975 | Lauber et al. . |
| 3,955,565 | 5/1976 | Johnson, Jr. . |
| 4,019,506 | 4/1977 | Eschmann . |
| 4,041,941 | 8/1977 | Driver . |
| 4,188,943 | 2/1980 | Sjöstrand . |
| 4,235,228 | 11/1980 | Gaylord, Jr. et al. . |
| 4,279,344 | 7/1981 | Holloway, Jr. . |
| 4,280,489 | 7/1981 | Johnson, Jr. . |
| 4,287,920 | 9/1981 | Johnson, Jr. . |
| 4,411,262 | 10/1983 | von Bonin et al. . |
| 4,427,002 | 1/1984 | Baron et al. . |

(List continued on next page.)

OTHER PUBLICATIONS

Cutter Biomedical, Immobilizer, pp. 1–4, Jan., 1982, Cutter Laboratories, Inc.

"Plaster Splints Aren't What They're Cracked Up to Be," Eudurasplint brochure, Carapace Inc, (1987).

Universal Plaster Splinting, Universal Plaster Splinting System, pp. 1–7, 1986, Zimmer, Inc.

Scotchcast 2 Splinting System (Undated) (Orthopedic Products Division, Minnesota Mining & Manufacturing Company).

Primary Examiner—Linda C. Dvorak
Attorney, Agent, or Firm—Adams Law Firm, P.A.

[57] ABSTRACT

An ankle brace product including an ankle brace for being custom-formed to the shape of an ankle while flexible and upon hardening providing a rigid, supporting custom fit. The ankle brace product includes an outer container formed of moisture-impervious material and a flexible ankle brace positioned in the container in substantially moisture-free conditions and sealed therein against entry of moisture until use. The ankle brace includes an elongate substrate with a reactive system impregnated into or coated onto the substrate. The system remains stable when maintained in substantially moisture-free conditions and hardens upon exposure to moisture to form a rigid, self supporting structure. An elongate, flexible protective pad is positioned on one side of the substrate along its length to provide a cushioning barrier between the substrate and the skin of a patient when the ankle brace is in use. An outer wrapping encloses the substrate and the protective pad. Alternatively, the outer wrapping covers the substrate and the pad provides protection on the other side of the brace next to the skin. The substrate, protective pad and outer wrapping define a first brace segment for being molded while flexible to the lateral aspect of the foot, ankle and lower leg, a second brace segment for being molded to the medial aspect of the foot, ankle and lower leg, and a heel support of reduced width in comparison with the first and second brace segments for supporting the heel and the molded first and second segments.

15 Claims, 6 Drawing Sheets

U.S. PATENT DOCUMENTS

| | | |
|---|---|---|
| 4,433,680 | 2/1984 | Yoon . |
| 4,442,833 | 4/1984 | Dahlen et al. . |
| 4,454,874 | 6/1984 | Monnier . |
| 4,502,479 | 3/1985 | Garwood et al. . |
| 4,570,622 | 2/1986 | von Bonin et al. . |
| 4,572,171 | 2/1986 | Wegner et al. . |
| 4,628,917 | 12/1986 | Campagna, Jr. et al. . |
| 4,628,945 | 12/1986 | Johnson, Jr. . |
| 4,676,861 | 6/1987 | Bishop . |
| 4,770,299 | 9/1988 | Parker . |
| 4,869,046 | 9/1989 | Parker . |
| 4,899,738 | 2/1990 | Parker . |
| 4,945,903 | 8/1990 | Alper . |
| 4,989,593 | 2/1991 | Campagna et al. . |
| 5,003,970 | 4/1991 | Parker et al. . |
| 5,016,622 | 5/1991 | Norvell . |
| 5,027,803 | 7/1991 | Scholz et al. . |
| 5,088,478 | 2/1992 | Grim . |
| 5,113,877 | 5/1992 | Johnson, Jr. et al. . |
| 5,125,400 | 6/1992 | Johnson, Jr. . |
| 5,213,564 | 5/1993 | Johnson, Jr. et al. . |
| 5,217,431 | 6/1993 | Toronto et al. . |
| 5,230,335 | 7/1993 | Johnson, Jr. et al. . |
| 5,277,695 | 1/1994 | Johnson, Jr. et al. . |
| 5,314,455 | 5/1994 | Johnson, Jr. et al. . |
| 5,330,419 | 7/1994 | Toronto et al. . |
| 5,368,549 | 11/1994 | McVicker . |
| 5,393,303 | 2/1995 | Shiono . |
| 5,449,005 | 9/1995 | Echols ............ 602/27 X |
| 5,456,658 | 10/1995 | Duback et al. ............ 602/8 |
| 5,501,659 | 3/1996 | Morris et al. ............ 602/27 |
| 5,544,663 | 8/1996 | Duback ............ 602/8 X |

CUSTOM-MOLDED ANKLE BRACE

TECHNICAL FIELD AND BACKGROUND OF THE INVENTION

This invention relates to a custom-fitted ankle brace.

The invention has particular application in the orthopedic medical field, where ankle sprains or fractures are often splinted with a brace so that the patient can continue to walk while the injury heals. One typical such injury is a sprain of the anterior talofibular ligament at the interior margin of the lateral malleolus. In such cases, it is essential to brace the ankle in such a way as to stabilize the ankle against eversion and inversion while permitting dorsiflexion and planoflexion necessary for normal walking and therapeutic exercise. It is also desirable for the brace to be sufficiently compact to fit within a conventional shoe. The invention takes advantage of polymer chemistry to permit quick and easy molding of a brace to the ankle. Shock attenuation is increased since the custom fit provides spreads contact between the brace and the ankle over a wider surface area.

Therefore, in the particular embodiment of the invention disclosed in this application, the brace will accommodate a wide range of sizes and can be fitted to either the right or left ankle. Thus, a much reduced inventory is required. This feature also substantially reduces design and manufacturing costs, and promotes use through ease of fitting.

Prior art ankle braces include numerous types of braces which typically include a soft component to place near the skin and a hard, shell-like preformed outer cover having a shape approximating a "normal" ankle. The soft component, for example, fiber padding, foam or and air bladder, is intended not only to provide a cushion, but also to accommodate itself to the varying configurations of differing sized and shaped body parts. For this reason, the cushioned part is substantially greater in thickness than required merely to provide the required amount of shock attenuation. Such devices are sufficiently "generic" in size and shape that they are usually required to be held in place by straps or bands.

Other prior art ankle braces include pads which are constructed of thermosetting materials, which are heated and then formed to the body while heated. These products require a source of heat, and are susceptible to either over-or-underheating, in addition, body heat itself can soften or increase the flexibility of the pad, thereby decreasing the effectiveness of the protection offered by the pad.

The present invention permits quick and easy application of an ankle brace to a body part in such a way as to achieve a true custom fit. The moisture curable resin system used results in a very rigid ankle brace which holds the shape of the molded brace to a very high degree. No heat is required, and a source of water is the only additional material necessary to achieve a cure. Atmospheric moisture alone will cure the brace into its hardened position in a relatively short period of time, but in practice the resin in or on the brace will typically be activated by dipping in water.

SUMMARY OF THE INVENTION

Therefore, it is an object of the invention to provide a ankle brace which can be molded to an ankle to stabilize the ankle against eversion and inversion while permitting dorsiflexion and planoflexion necessary for normal walking and therapeutic exercise.

It is another object of the invention to provide an ankle brace which can be custom-fitted to a particular patient.

It is another object of the invention to provide an ankle brace having a shape which permits the brace to be used on either the left or the right ankle.

It is another object of the invention to provide an ankle brace which hardens in the presence of moisture to form a very rigid but very lightweight brace.

It is another object of the invention to provide an ankle brace which can be worn without the need for the brace to be held into place by straps or belts.

It is another object of the invention to provide an ankle brace which can be worn inside a shoe.

It is another object of the invention to provide a ankle brace which is stored in a moisture-proof pouch until ready for application to the ankle.

It is another object of the invention to provide an ankle brace which provides a specific structure to provide enhanced comfort to the heel of the wearer.

These and other objects of the present invention are achieved in the preferred embodiments disclosed below by providing an ankle brace product including an ankle brace for being custom-formed to the shape of an ankle while flexible and upon hardening providing a rigid, supporting custom fit. The ankle brace product includes an outer container formed of moisture-impervious material and a flexible ankle brace positioned in the container in substantially moisture-free conditions and sealed therein against entry of moisture until use. The ankle brace includes an elongate substrate with a reactive system impregnated into or coated onto the substrate, the system remaining stable when maintained in substantially moisture-free conditions and hardening upon exposure to moisture to form a rigid, self supporting structure. An elongate, flexible protective pad is positioned on one side of the substrate along its length to provide a cushioning barrier between the substrate and the skin of a patient when the ankle brace is in use. An elongate outer wrapping encloses or covers at least the substrate. The substrate, protective pad and outer wrapping define a first brace segment for being molded while flexible to the lateral aspect of the foot, ankle and lower leg, a second brace segment for being molded while flexible to the medial aspect of the foot, ankle and lower leg, and a heel support of reduced width in comparison with the first and second brace segments. The heel support is positioned intermediate the first and second segments and is integral therewith for supporting the heel and the molded first and second segments.

According to one preferred embodiment of the invention, an ankle brace product is provided, including an ankle brace for being custom-formed to the shape of an ankle while flexible and upon hardening providing a rigid, supporting custom fit. The ankle brace product includes an outer container formed of moisture-impervious material and a flexible ankle brace positioned in the container in substantially moisture-free conditions and sealed therein against entry of moisture until use. The ankle brace includes an elongate substrate with a reactive system impregnated into or coated onto the substrate, the system remaining stable when maintained in substantially moisture-free conditions and hardening upon exposure to moisture to form a rigid, self supporting structure. An elongate, flexible protective pad is positioned on one side of the substrate along its length to provide a cushioning barrier between the substrate and the skin of a patient when the ankle brace is in use. An elongate outer wrapping encloses the substrate and the protective pad. The substrate, protective pad and outer wrapping define a first brace segment for being molded while flexible to the lateral aspect of the foot, ankle and lower leg, a second brace segment for being molded while flexible to the medial aspect of the foot, ankle and lower leg, and a heel support of reduced thickness in comparison with the first and second brace segments. The heel support is positioned intermediate the first and second segments and is integral therewith for supporting the heel and the molded first and second segments.

According to one preferred embodiment of the invention wherein the heel support is of reduced width, the heel support also has a reduced thickness in comparison with the first and second brace segments.

According to one preferred embodiment of the invention wherein the heel support is of reduced thickness, the heel support also has a reduced width in comparison with the first and second brace segments.

According to another preferred embodiment of the invention, the container is fabricated of a aluminum foil laminate having an outer tear resistant layer, a central aluminum foil layer and an inner heat sealable plastic layer.

According to yet another preferred embodiment of the invention, the substrate comprises a plurality of knitted or woven fabric layers.

According to yet another preferred embodiment of the invention, the protective pad comprises a foam material.

Preferably, the foam material is chosen from the group consisting of open or closed cell EVA or polyurethane.

According to yet another preferred embodiment of the invention, the elongate outer wrapping encloses the substrate and the pad and the elongate outer wrapping is a fabric.

Preferably, the fabric is chosen from the group consisting of woven, knitted or non-woven fabric formed from synthetic, hydrophobic fibers.

Preferably, the reactive system comprises a blended polyisocyanate, polyol, catalyst and stabilizer.

According to yet another preferred embodiment of the invention, the substrate in the first and second brace segments includes at least three layers of fabric and the substrate in the heel support includes at least two layers of fabric to provide the reduced thickness to the heel support.

According to yet another preferred embodiment of the invention, the substrate in the first and second brace segments comprises at least five layers of fabric and the substrate in the heel support comprises at least three but less than five layers of fabric.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
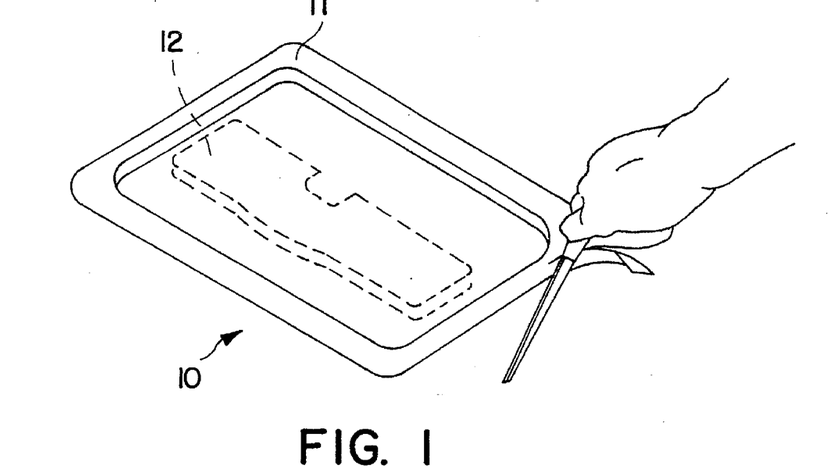
FIG. 1 illustrates the ankle brace product and the removal of the ankle brace from the protective pouch.

Referring now specifically to the drawings, an ankle brace product according to a preferred embodiment of the invention is illustrated broadly at reference numeral 10. A sealed, moisture-impervious foil and plastic laminated container 11 is fabricated of a aluminum foil laminate having an outer tear resistant layer, a central aluminum foil layer and an inner heat sealable plastic layer. Container 11 is opened with scissors or a knife, and an ankle brace 12 (see FIG. 2) according to an embodiment of the invention is removed.

Ankle brace 12 is preferably integrally formed in a single length and includes first and second brace segments 13 and 14. As viewed in FIG. 2, the brace segment 13 is formed to the lateral aspect of the ankle and lower leg and brace segment 14 is formed to the medial aspect of the ankle and lower leg.

Figure 2:
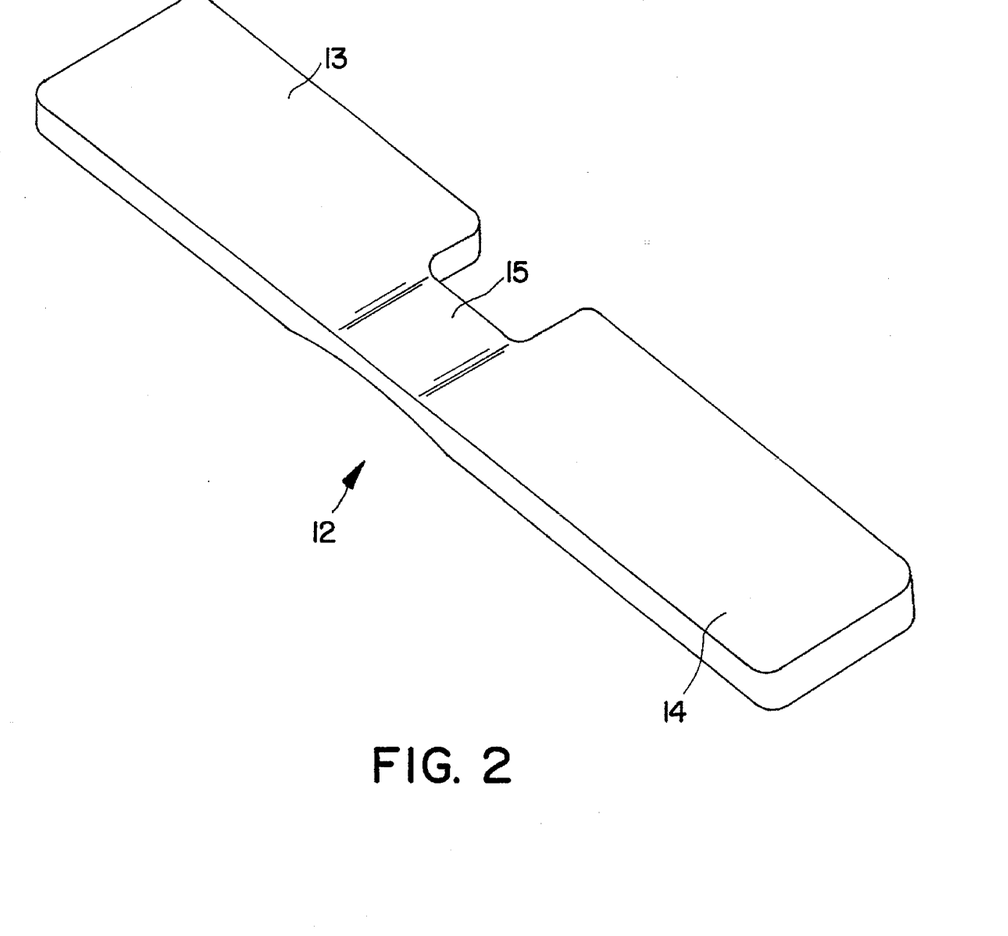
FIG. 2 is a perspective view showing the ankle brace according to an embodiment of the invention.

Ankle brace 12 also includes a heel support 15 of reduced thickness and width which is formed between first and second brace segments 13 and 14 and which rests under the heel of the wearer when the ankle brace 12 is properly applied. These features are more fully explained and illustrated below.

Figure 3:
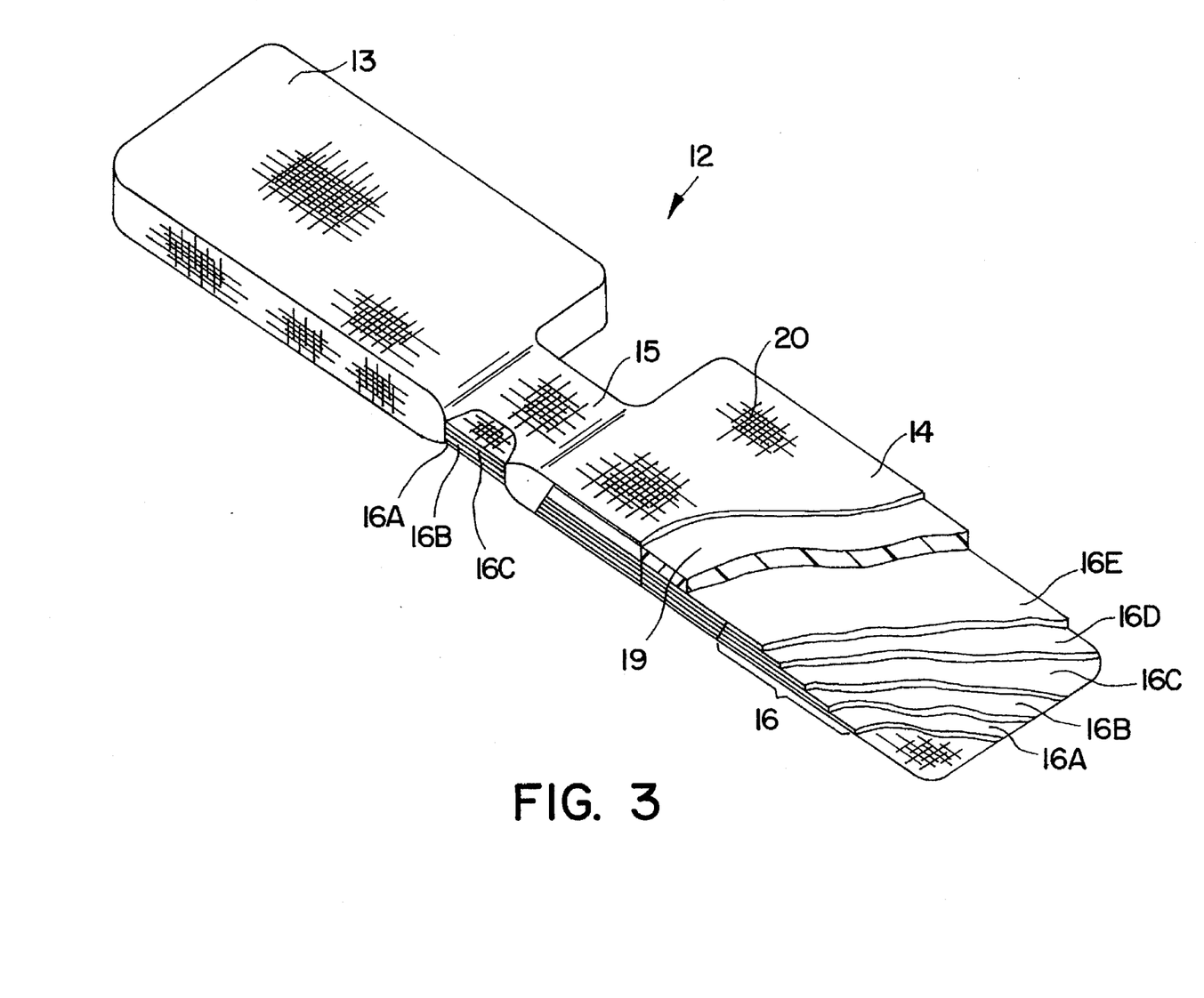
FIG. 3 is a perspective view according to FIG. 1 with parts broken away for clarity.

Referring now to FIG. 3, ankle brace 12 is illustrated and described more specifically. Ankle brace 12 includes a multilayer substrate 16 formed of, for example, five layers of woven fiberglass fabric 16A–E overlaid in registration with each other to form a relatively thick structure in the area of the segments 13 and 14, and, for example, three layers of fiberglass 16A–C in the area of the heel support 15. This construction is formed by using a continuous length of fiberglass fabric for the layers 16A–C, while the layers 16D–E are discontinuous. This construction substantially reduces the thickness of the heel support 15.

Other fabric material and constructions, such as knitted polypropylene, can also be used for the substrate fabric.

The fiberglass fabric layers 16A–E of the substrate 16 are impregnated or coated with a moisture-curable resin such as polyisocyanate as described in full in the present applicant's U.S. Pat. No. 4,770,299. This reactive system remains stable when maintained in substantially moisture-free conditions, such as in the moisture-impervious pouch 11, but hardens upon exposure to sufficient moisture to form a rigid, self-supporting structure. A typical formulation of the reactive system is set forth in the following table:

Typical Formulation:

| Isonate ↓ 143L | or | | |
|---|---|---|---|
| Mondur ↓ CD | or | polyisocyanate | 50.0% |
| Rubinate ↓ XI168 | | | |

-continued

| | | |
|---|---|---|
| Pluracol ↓ P1010 | polyol | 46.6% |
| DC-200 Silicone | defoaming agent | 0.30% |
| Benzoyl Chloride | stabilizer | 0.10% |
| Thancat ↓ DM-70 | catalyst | 3.0% |
| | | 100% |

A complete discussion of the parameters of the reactive system, the manner of production and the variables which apply are found in U.S. Pat. No. 4,411,262.

The polyisocyanate resin remains in a viscous, liquid unhardened state so long as the resin is not exposed to moisture. This permits the fiberglass layers 16A–E to remain flexible and moldable so long as the resin is not exposed to moisture, and for a relatively short period of time after exposure to moisture. The curing time can be controlled to some extent by the quantity of water to which the resin is exposed. For example, exposure to water by dipping will result in quite rapid curing, while merely allowing the resin to be exposed to air will cause long curing times proportional to the amount of moisture in the air to which it is exposed.

Fiberglass layers 16A–E are covered with a foam protective pad 19, which may be a single thickness or a laminated structure. One preferred embodiment is a ⅜ inch, six pound EVA (ethylene vinyl acetate) pad. Another embodiment may be a ⅜ inch laminated pad of a ⅛ inch outer EVA pad and a ¼ inch outer polyethylene/polyurethane, combination open and closed cell foam.

The pad 19 provides cushioning between the skin and the rigid substrate 16. The foam layer 19 is flexible enough to bend easily with the other components of the ankle brace 12 during fitting and curing. The pad 19 extends the entire length of the ankle brace 12, including the area of the heel support 15.

A fabric outer wrapping 20, such as a knitted polypropylene fabric, completely encloses the substrate 16 and the foam pad 19. The wrapping provides further protection to the skin and reduces friction on the foam pad 19, which is susceptible to wear in the presence of high friction conditions. The polypropylene fabric, being hydrophobic, also promotes dryness next to the skin and therefore discourages itching, rashes and infection.

Alternatively, the outer wrapping 20 can be constructed to cover only the substrate 16, with the foam pad itself protecting the opposite side. In this embodiment, the outer wrapping, for example, a knitted polypropylene fabric, is sewn with, for example, a serging seam directly to the edges of the foam pad 19 enclosing the substrate 16.

Figure 4:
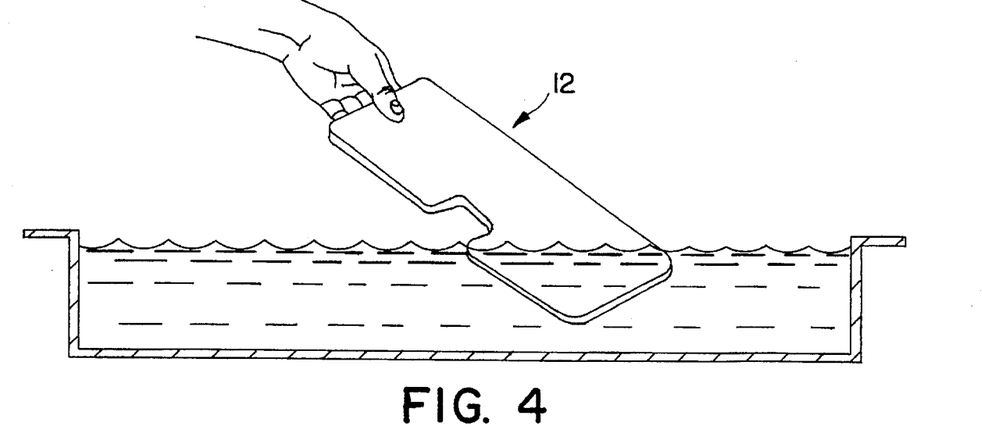
FIG. 4 illustrates that the ankle brace is wetted in water before application.

Referring now to FIGS. 4–11, preparation and application of the ankle brace 12 is illustrated. In FIG. 4, the ankle brace 12 has just been removed from the protective container 11 and is dipped in water to activate the moisture-curable resin described above.

Figure 5:
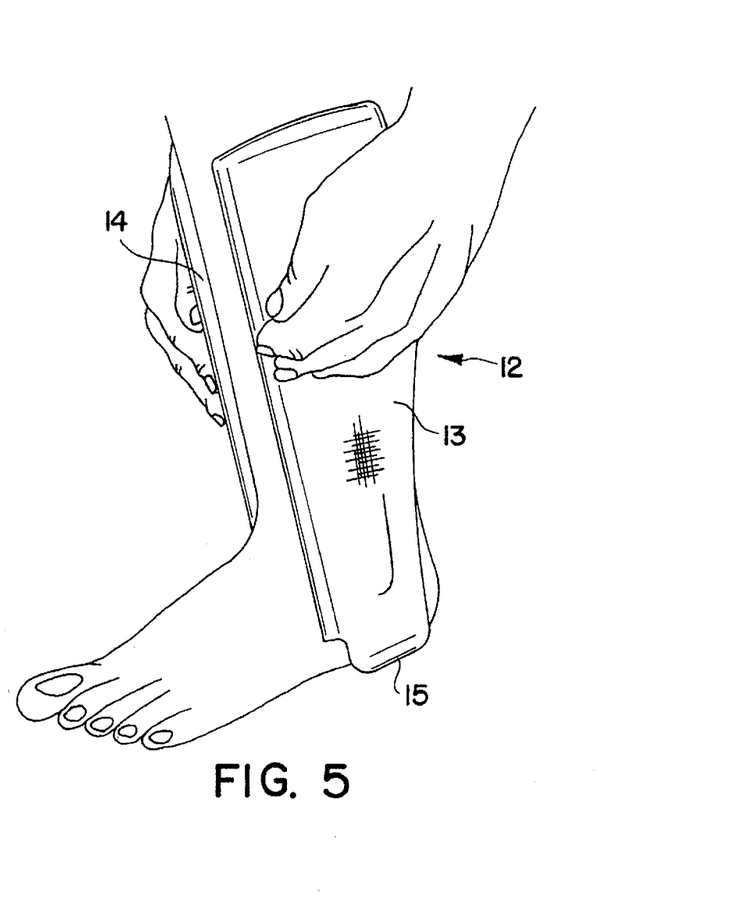
FIG. 5 is a perspective view illustrating application of the wetted ankle brace to the ankle.

As shown in FIG. 5, the wetted and still flexible ankle brace 12 is placed on the foot by positioning the heel of the patient directly onto the heel support 15 with the recess in the heel support facing towards the front of the foot, and then flexing the ankle brace 12 upwardly along the lateral and medial aspects of the lower leg, so that the brace segments 13 and 14 are positioned as shown. See also FIG. 6.

Figures 8, 9:
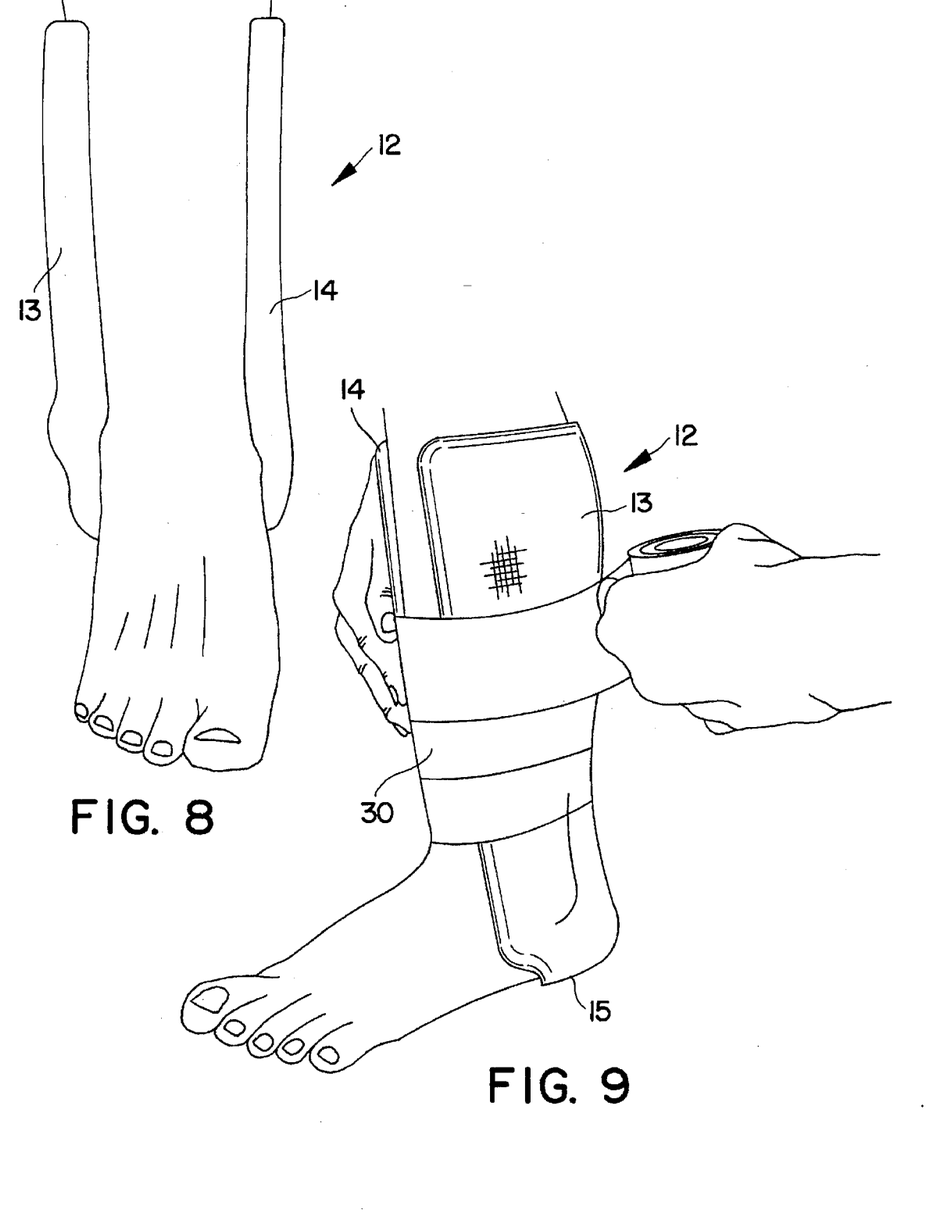
FIG. 8 is a front elevation of the ankle brace in place on the ankle.
FIG. 9 is a perspective view showing that the ankle brace may be wrapped to hold it in place during curing and during wear.

Note that ankle brace 12 is usable on either the right or left foot. Since the recess in the heel support 15 always faces forward, the brace segment 13 will be placed on the lateral aspect and the brace segment 14 on the medial aspect of the left foot, as shown in FIGS. 5, 6 and 8. The brace segment 13 will be placed on the medial aspect and the brace segment 14 on the lateral aspect of the right foot, as shown in FIG. 7.

The ankle brace 12 is held in place so that as the curing takes place the exact conformation of the ankle and leg is transferred to the ankle brace 12. The ankle brace 12 will harden within a matter of minutes, and will permanently retain the conformation in which it was held during curing. Then, any overwrapping used to hold the ankle brace 12 in place may be removed. This process is a nonreversible chemical reaction, not a thermosetting process whereby a thermoplastic material is heated and then molded.

Figures 6, 7:
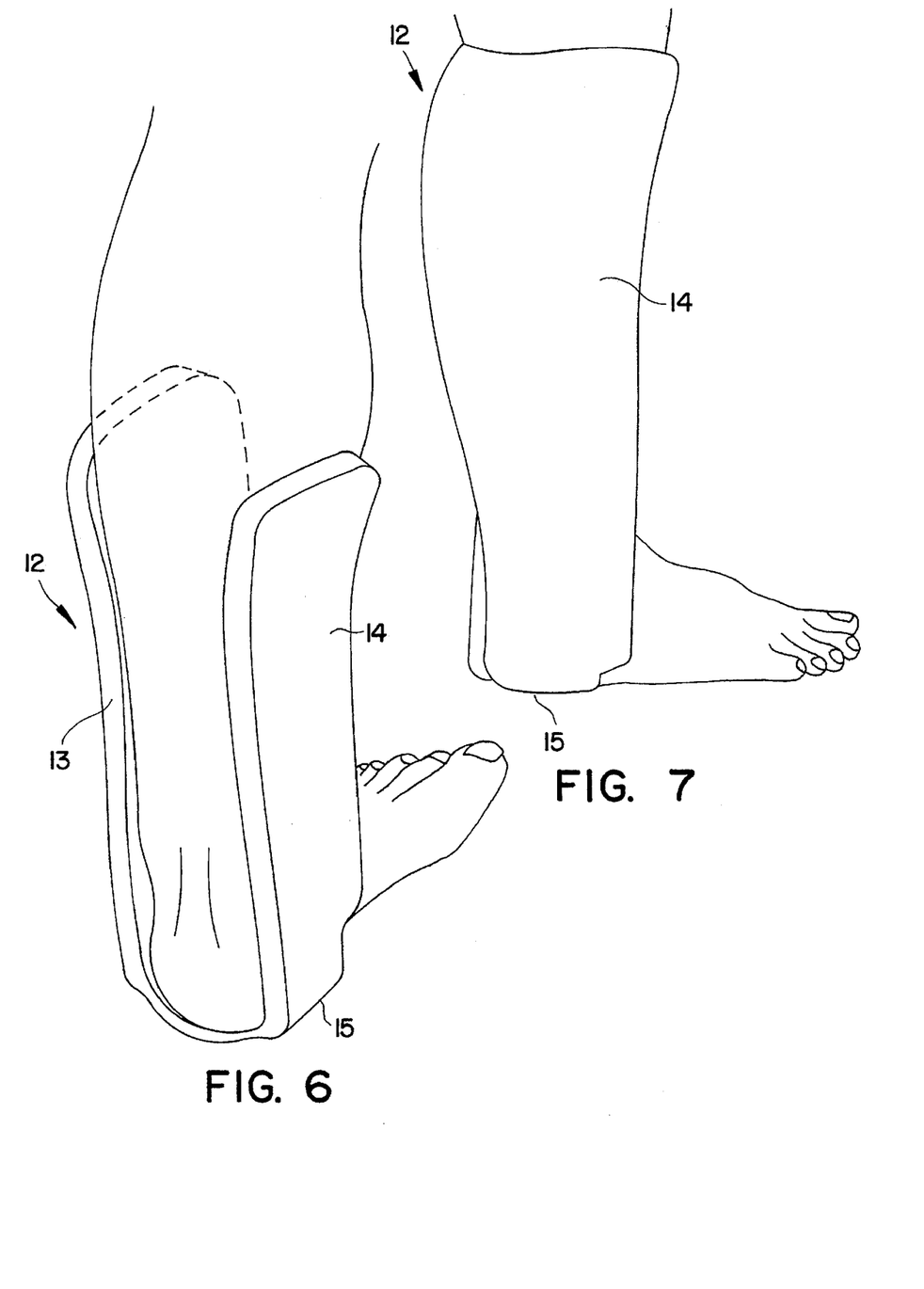
FIG. 6 is a perspective view illustrating the ankle brace in place on the ankle from the rear.
FIG. 7 is a side elevation of the ankle brace in place on the ankle.

As is best shown in FIG. 7, the reduced width of the heel support 15 eliminates that portion of the ankle brace 12 which would otherwise reside in the arch of the foot on the medial side, but which would cut into the side and bottom of the foot on the lateral side. This provides greater comfort to the patient, particularly when the braced foot is put into a shoe.

As is shown in FIGS. 6 and 8, a properly applied ankle brace 12 braces the medial and lateral aspects of the ankle and foot with minimal coverage of the front or rear of the foot or leg. Thus, eversion and inversion of the foot is prevented while permitting substantially unrestricted dorsiflexion and planoflexion necessary for normal walking and therapeutic exercise, and an enhanced ability to place the foot into a normal shoe. Typically, a relatively soft shoe, such as an athletic shoe will accommodate the ankle brace 12 easily, it being necessary only to loosen the laces to permit the added width to the shoe.

As is shown in FIG. 9, the ankle brace 12 may be held in place during curing by a wrapping, such as a conventional elastic medical bandage 30. Such a bandage may also be worn during treatment as a way of maintaining a close fit of the ankle brace 12 against the foot and leg.

Figure 10:
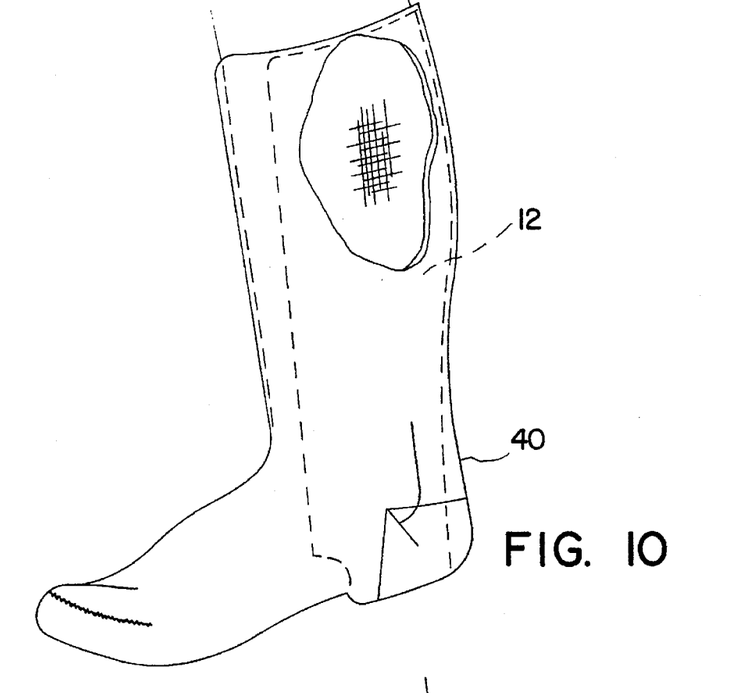
FIG. 10 is a perspective view, with parts broken away for clarity, of the ankle brace being worn under a sock.

A sock may also be used to hold the ankle brace 12 in place during hardening and during treatment, as is shown in FIG. 10.

Figure 11:
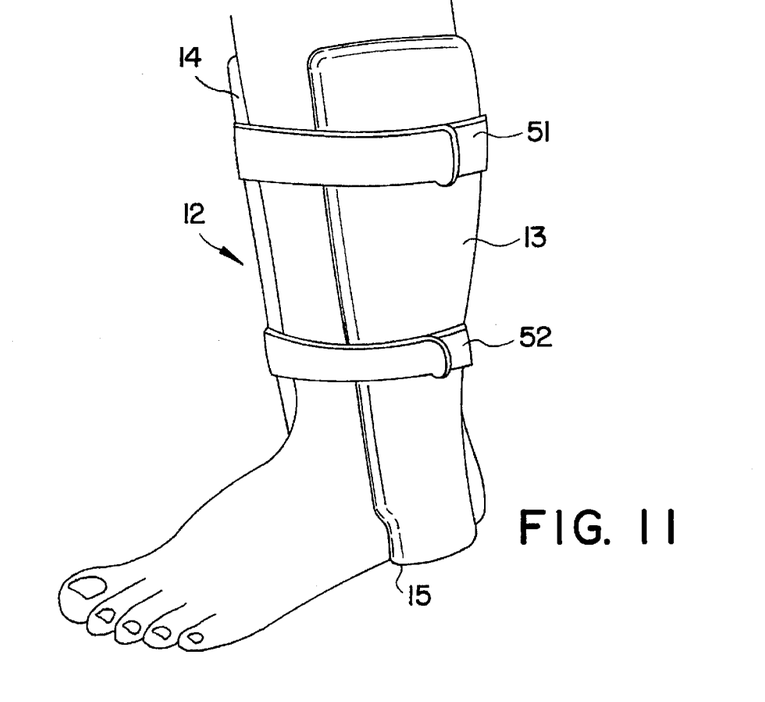
FIG. 11 is a perspective view showing that the ankle brace may be held in place with straps during curing and during wear.

Finally, straps such as elastic straps or straps with hook and loop fasteners such as straps 51 and 52, may be used to hold the ankle brace 12 in place during hardening and during treatment, as is shown in FIG. 11. These straps preferably may be separate elements as straps 51 and 52, or may be sewn onto the ankle brace 12 during manufacture.

In one preferred embodiment, the ankle brace 12 has an overall length of between 18 and 22 inches, and an overall width of 2.5 inches at the heel support 15 and of 4 inches on the brace segments 13 and 14. The approximate thickness of the ankle brace 12 of the heel support 15 is 0.3 inch, and of the brace segments, 0.5–0.6 inch.

An ankle brace is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. An ankle brace product including an ankle brace for being custom-formed to the shape of an ankle while flexible and upon hardening providing a rigid, supporting custom fit, said ankle brace product comprising:
    (a) an outer container formed of moisture-impervious material;
    (b) a flexible ankle brace positioned in the container in substantially moisture-free conditions and sealed therein against entry of moisture until use, the ankle brace comprising:

7

(i) an elongate substrate;
(ii) a reactive system impregnated into or coated onto the substrate, the system remaining stable when maintained in substantially moisture-free conditions and hardening upon exposure to moisture to form a rigid, self supporting structure;
(iii) an elongate, flexible protective pad positioned on one side of the substrate along its length to provide a cushioning barrier between the substrate and the skin of a patient when the ankle brace is in use;
(iv) an elongate outer wrapping covering at least the substrate; and
(v) said substrate, protective pad and outer wrapping defining a first brace segment for being molded while flexible to the lateral aspect of the foot, ankle and lower leg, a second brace segment for being molded while flexible to the medial aspect of the foot, ankle and lower leg, and a heel support of reduced width in comparison with the first and second brace segments, said heel support positioned intermediate said first and second segments and integral therewith for supporting the heel and the molded first and second segments.

2. An ankle brace product including an ankle brace for being custom-formed to the shape of an ankle while flexible and upon hardening providing a rigid, supporting custom fit, said ankle brace product comprising:

(a) an outer container formed of moisture-impervious material;
(b) a flexible ankle brace positioned in the container in substantially moisture-free conditions and sealed therein against entry of moisture until use, the ankle brace comprising:
  (i) an elongate substrate;
  (ii) a reactive system impregnated into or coated onto the substrate, the system remaining stable when maintained in substantially moisture-free conditions and hardening upon exposure to moisture to form a rigid, self supporting structure;
  (iii) an elongate, flexible protective pad positioned on one side of the substrate along its length to provide a cushioning barrier between the substrate and the skin of a patient when the ankle brace is in use;
  (iv) an elongate outer wrapping covering at least the substrate; and
  (v) said substrate, protective pad and outer wrapping defining a first brace segment for being molded while flexible to the lateral aspect of the foot, ankle and lower leg, a second brace segment for being molded while flexible to the medial aspect of the foot, ankle and lower leg, and a heel support of reduced thickness in comparison with the first and second brace segments, said heel support positioned intermediate said first and second segments and integral therewith for supporting the heel and the molded first and second segments.

3. An ankle brace product according to claim 1, wherein said heel support has a reduced thickness in comparison with the first and second brace segments.

4. An ankle brace product according to claim 2, wherein said heel support has a reduced width in comparison with the first and second brace segments.

5. An ankle brace product according to claim 1 or 2, wherein the container is fabricated of an aluminum foil laminate having an outer tear resistant layer, a central aluminum foil layer and an inner heat sealable plastic layer.

6. An ankle brace product according to claim 1 or 2, wherein the substrate comprises a plurality of knitted or woven fabric layers.

8

7. An ankle brace product according to claim 1 or 2, wherein the protective pad comprises a foam material.

8. An ankle brace product according to claim 7, wherein the foam material is chosen from the group consisting of open or closed cell EVA or polyurethane.

9. An ankle brace product according to claim 1 or 2, wherein the elongate outer wrapping encloses both the substrate and the pad.

10. An ankle brace product according to claim 9, wherein the fabric is chosen from the group consisting of woven, knitted or non-woven fabric formed from synthetic, hydrophobic fibers.

11. An ankle brace product according to claim 1 or 2, wherein the reactive system comprises a blended polyisocyanate, polyol, catalyst and stabilizer.

12. An ankle brace product according to claim 2 or 3, wherein the substrate in the first and second brace segments comprises at least three layers of fabric and the substrate in the heel support comprises at least two layers of fabric to provide the reduced thickness to the heel support.

13. An ankle brace product according to claim 12, wherein the substrate in said first and second brace segments comprises at least five layers of fabric and the substrate in the heel support comprises at least three but less than five layers of fabric.

14. An ankle brace for being custom-formed to the shape of an ankle while flexible and upon hardening providing a rigid, supporting custom fit, said ankle brace comprising:

(a) an elongate substrate;
(b) a reactive system impregnated into or coated onto the substrate, the system remaining stable when maintained in substantially moisture-free conditions and hardening upon exposure to moisture to form a rigid, self supporting structure;
(c) an elongate, flexible protective pad positioned on one side of the substrate along its length to provide a cushioning barrier between the substrate and the skin of a patient when the ankle brace is in use;
(d) an elongate outer wrapping enclosing at least the substrate; and
(e) said substrate, protective pad and outer wrapping defining a first brace segment for being molded while flexible to the lateral aspect of the foot, ankle and lower leg, a second brace segment for being molded while flexible to the medial aspect of the foot, ankle and lower leg, and a heel support of reduced width in comparison with the first and second brace segments, said heel support positioned intermediate said first and second segments and integral therewith for supporting the heel and the molded first and second segments.

15. An ankle brace for being custom-formed to the shape of an ankle while flexible and upon hardening providing a rigid, supporting custom fit, said ankle brace comprising:

(a) an elongate substrate;
(b) a reactive system impregnated into or coated onto the substrate, the system remaining stable when maintained in substantially moisture-free conditions and hardening upon exposure to moisture to form a rigid, self supporting structure;
(c) an elongate, flexible protective pad positioned on one side of the substrate along its length to provide a cushioning barrier between the substrate and the skin of a patient when the ankle brace is in use;
(d) an elongate outer wrapping enclosing at least the substrate; and
(e) said substrate, protective pad and outer wrapping defining a first brace segment for being molded while flexible to the lateral aspect of the foot, ankle and lower leg, a second brace segment for being molded while flexible to the medial aspect of the foot, ankle and lower leg, and a heel support of reduced thickness in comparison with the first and second brace segments, said heel support positioned intermediate said first and second segments and integral therewith for supporting the heel and the molded first and second segments.

* * * * *